(12) United States Patent
Guo (10) Patent No.: US 6,689,088 B2
(45) Date of Patent: Feb. 10, 2004

(54) IRRIGATOR USED IN CELIOSCOPE SURGERY

(76) Inventor: Qi-Zhao Guo, 235 Chung - Ho Box 8-24, Taipei (TW)

( * ) Notice: Subject to any disclaimer, the term of this patent is extended or adjusted under 35 U.S.C. 154(b) by 0 days.

(21) Appl. No.: 10/025,420

(22) Filed: Dec. 26, 2001

(65) Prior Publication Data

US 2003/0120203 A1 Jun. 26, 2003

(51) Int. Cl.[7] .............................. A61M 1/00; A61M 5/00
(52) U.S. Cl. .......................... 604/27; 604/119; 604/249
(58) Field of Search .............................. 604/27–30, 119, 604/236, 249, 33, 181, 82, 32, 35, 237; 600/159–154

(56) References Cited

U.S. PATENT DOCUMENTS

| | | | |
|---|---|---|---|
| 4,270,525 A | * | 6/1981 | Furihata ................ 235/462.16 |
| 5,125,910 A | * | 6/1992 | Freitas ........................ 604/249 |
| 5,312,373 A | * | 5/1994 | Freitas ........................ 604/249 |
| 5,902,264 A | * | 5/1999 | Toso et al. ..................... 604/27 |

* cited by examiner

*Primary Examiner*—Michael J. Hayes
*Assistant Examiner*—Roz Ghafoorian (57) ABSTRACT

An irrigator used in a celioscope surgery comprises a main casing, a water pumping stud and a water control stud which are engaged with the main casing. An interior of the main casing has a pumping opening and a suction opening, and a water outlet channel and a pumping flow channel which are vertical to the pumping opening and suction opening. Thereby, the water outlet channel and pumping flow channel are at an upper portion of the main casing. Thereby, dirty water accumulated in the affected part can be pumped out from a water outlet tube through the pumping flow channel. Since the water is pumped out along a straight way, it is prevented that dirty water is left in some bending portions. Therefore, dirty water can be pumped out completely. Furthermore, users may hold it by any hand conveniently.

2 Claims, 8 Drawing Sheets

IRRIGATOR USED IN CELIOSCOPE SURGERY

BACKGROUND OF THE INVENTION

1. Field of the Invention

The present invention relates to irrigators, and particularly to an irrigator used in a celioscope surgery for preventing that dirty water is left in some bending portions. Therefore, dirty water can be pumped out completely.

2. Description of Related Art

An irrigator used in a celioscope surgery serves for pumping blood of a patient so as to sustain the cleanness of the surgical portion and thus the affected part can be viewed clearly.

Figure 5:
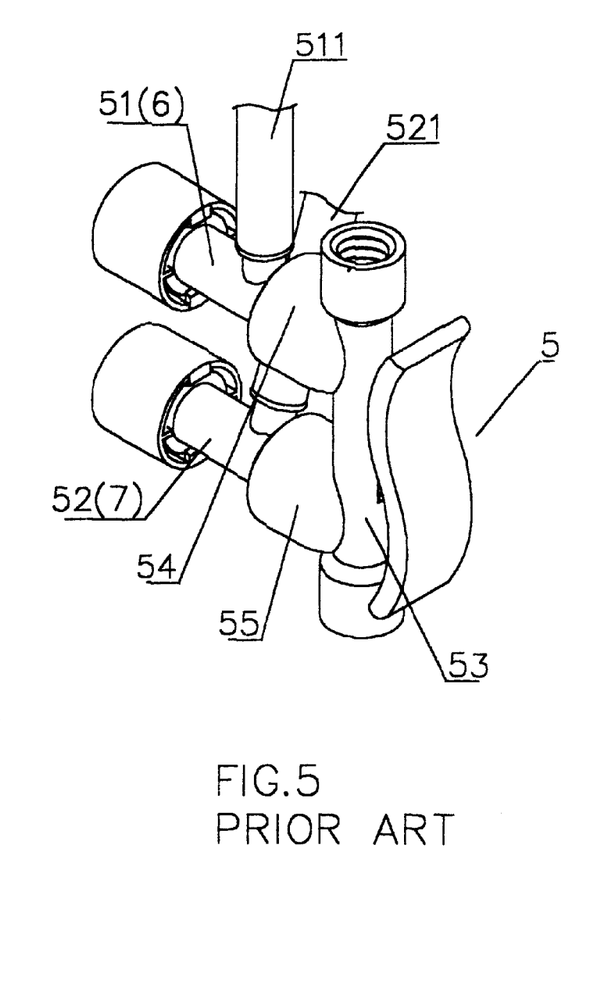
FIG. 5 is a perspective view of a prior art.
Figure 6:
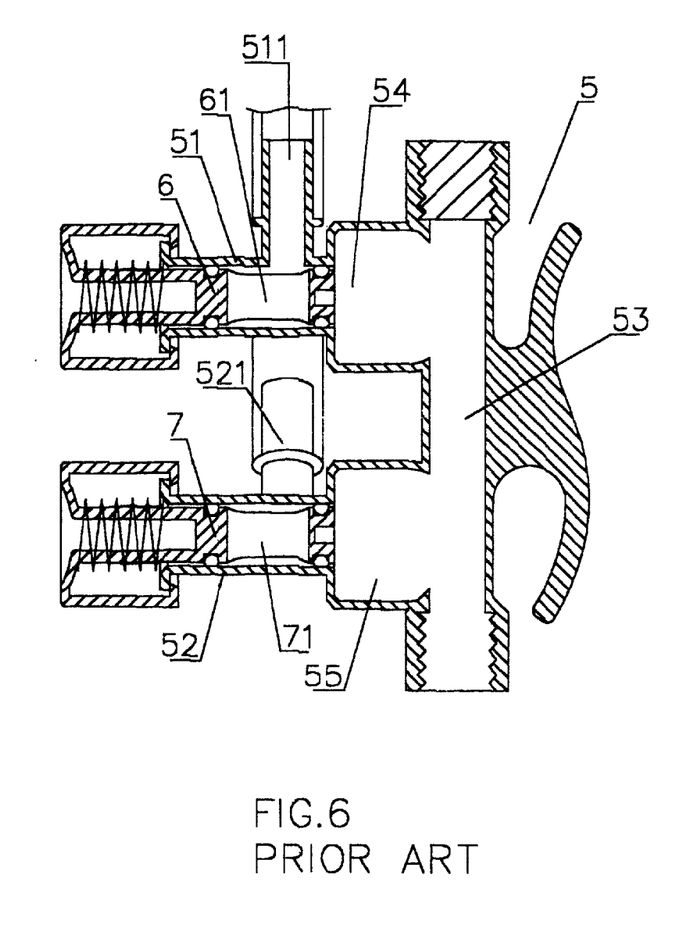
FIG. 6 is a plane view of the prior art.

FIGS. 5 and 6 shows a prior art irrigator. The irrigator is formed by a main casing 5 having a pumping opening 51 and a suction opening 52 which are engaged with the water pumping stud 6 and the water control stud 7, respectively, above the pumping opening 51 and the suction opening 52 of the main casing 5.

The main casing 5 has a water outlet channel 53 which is vertical to the pumping opening 51 and suction opening 52. The portion conducting the water outlet channel 53 and the pumping opening 51 has a pumping region 54 with a large diameter, and the portion conducting the water outlet channel 53 and the suction opening 52 has an outlet region 55 with a large diameter. The main casing 5 has a water inlet channel 521 installed above the suction opening 52. Thereby, when the water control stud 7 is pressed, the guide hole 71 of the water control stud exactly forms a flow guide channel with the outlet region 55. Thereby, water may flow through the water outlet channel 53 to the affected part of a patient. The main casing 5 has a pumping flow channel 511 above the pumping opening 51. Thereby, the via hole 61 of the water pumping stud 6 can be aligned with the pumping region 54 for pumping the water in the affected region.

In practical use, the irrigator is not an ideal device because of the following reasons:

1. It can not pump blood completely: since the water outlet channel 53 of the main casing 5 is not a straight one and in fact it passes through a bending portion at an top of the water outlet channel (i.e., the pumping region 54), then the water passes through the second bending portion. Thereby, the impact of the blood is reduced and thus some dirty material may remain in the pipe. Especially at the connection of the water outlet channel 53 and the suction opening 52 (i.e., outlet region 55). Since it cover a larger range, as the pumping pressure is not sufficient, it may enter this region so as to become a blind spot. Therefore, when the user presses the water control stud 7 again for conducting water flow, water (or blood) will remain in this outlet region 55 and then returns to the affected part of the patient so that the bacteria in the blood returns. As a result, the polluted area is enlarged.

2. It can not be held by only one hand

Since the prior art irrigator has pumping flow channel 511 and water inlet channel 521 at the tops of the pumping opening 51 and the suction opening 52. Moreover, since the pumping opening 51 and the suction opening 52 are at the same horizontal plane. Therefore, the water inlet flow is slightly bent so as to separate from the pumping flow channel 511. Therefore, the water inlet channel protrudes out of the main casing so that as the user holds it and presses it. The palm thereof exactly resists against the water inlet channel 521. If the force applied is improper, it is possible that the water inlet channel 521 is pressed by an overlarge force so that the blood or water can not flow successfully. Therefore, the user must hold it by left hand and it induces a convenience in surgery.

SUMMARY OF THE INVENTION

Accordingly, the primary object of the present invention is to provide an irrigator used in a celioscope surgery, wherein the irrigator used comprises a main casing, a water pumping stud and a water control stud which are engaged with the main casing. An interior of the main casing has a pumping opening and a suction opening, and a water outlet channel and a pumping flow channel which are vertical to the pumping opening and suction opening. Thereby, the water outlet channel and pumping flow channel are at an upper portion of the main casing. Thereby, dirty water accumulated in the affected part can be drawn out from a water outlet tube through the pumping flow channel. Since the water is pumped out straightly, the dirty water is prevented from leaving in some bending portions. Therefore, dirty water can be pumped out completely.

Another object of the present invention is to provide an irrigator used in a celioscope surgery, wherein the water outlet channel and the pumping flow channel are above the main casing. Thus, user may hold it by any hand conveniently. Therefore, the user may use the present invention by any one of the two hands alternatively.

The various objects and advantages of the present invention will be more readily understood from the following detailed description when read in conjunction with the appended drawing.

BRIEF DESCRIPTION OF THE DRAWINGS

FIG. 3-A is a plane view showing one embodiment of the present invention which is in a normal condition.

FIG. 3-B is a plane view showing that water is supplied according to the present invention.

FIG. 3-C is a plane view showing one embodiment of the present invention wherein water is pumped out.

DETAILED DESCRIPTION OF THE PREFERRED EMBODIMENTS

Figure 1:
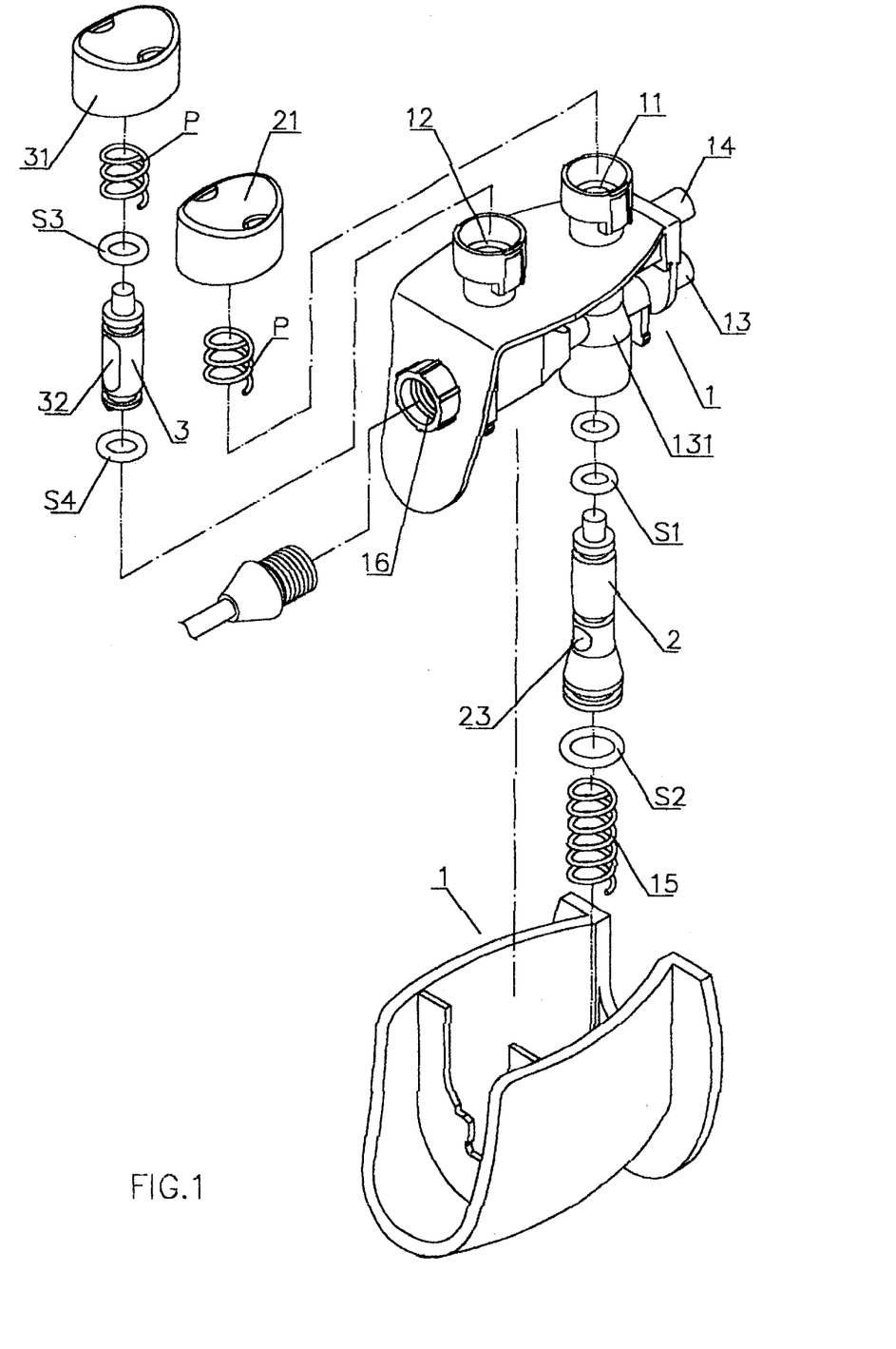
FIG. 1 is an exploded perspective view of the present invention.
Figure 2:
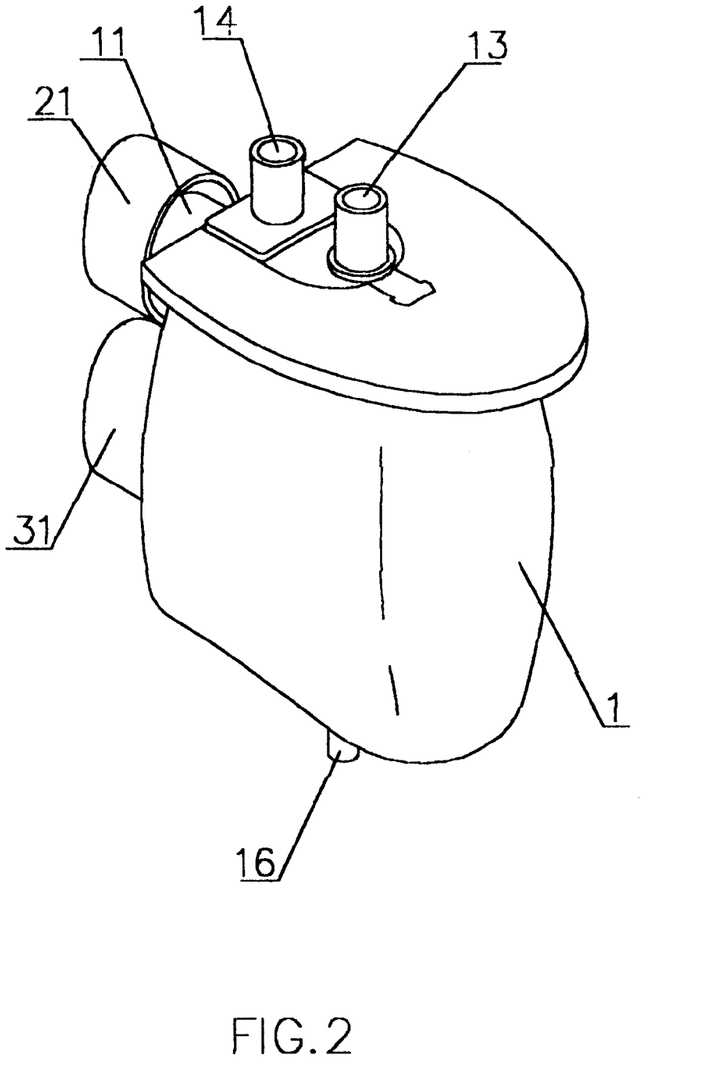
FIG. 2 is a perspective view of the present invention.

Referring to FIGS. 1 and 2, the structure of the present invention is clearly illustrated. The present invention mainly comprises a main casing 1 having a pumping opening 11 and a suction opening 12, a water pumping stud 2 engaged with the pumping opening 11 of the main casing 1 and a water control stud 3 engaged with the suction opening 12 of the main casing 1.

The main casing 1 has a pumping flow channel 13 vertically conducted with the pumping opening 11 and a water outlet channel 14 vertically conducted with the suction opening 12. The water outlet channel 14 is connected to an external pump for providing pressure to inlet water. The pumping flow channel 13 is externally connected to another pump for pumping flow. The connection of the pumping flow channel 13 and the pumping opening 11 has a funnel shaped via hole 131 for tightening the tightening portion 22 of the water pumping stud 2. Thereby, in normal condition, the water pumping stud 2 resists against an elastomer 15 so as to seal the pumping flow channel 13. An end of the pumping flow channel 13 has a straight water outlet tube 16 which is straightly connected to the pumping flow channel 13.

A forefront of the water pumping stud 2 engaged with the pumping opening 11 of the main casing 1 has a button 21 and water control stud 3 engaged with the suction opening 12 of the main casing 1 has a button 31. Springs P are placed between the buttons and the studs. Thereby, after the button is pressed, it can restore by the resilient force of the spring P.

Figure 3:
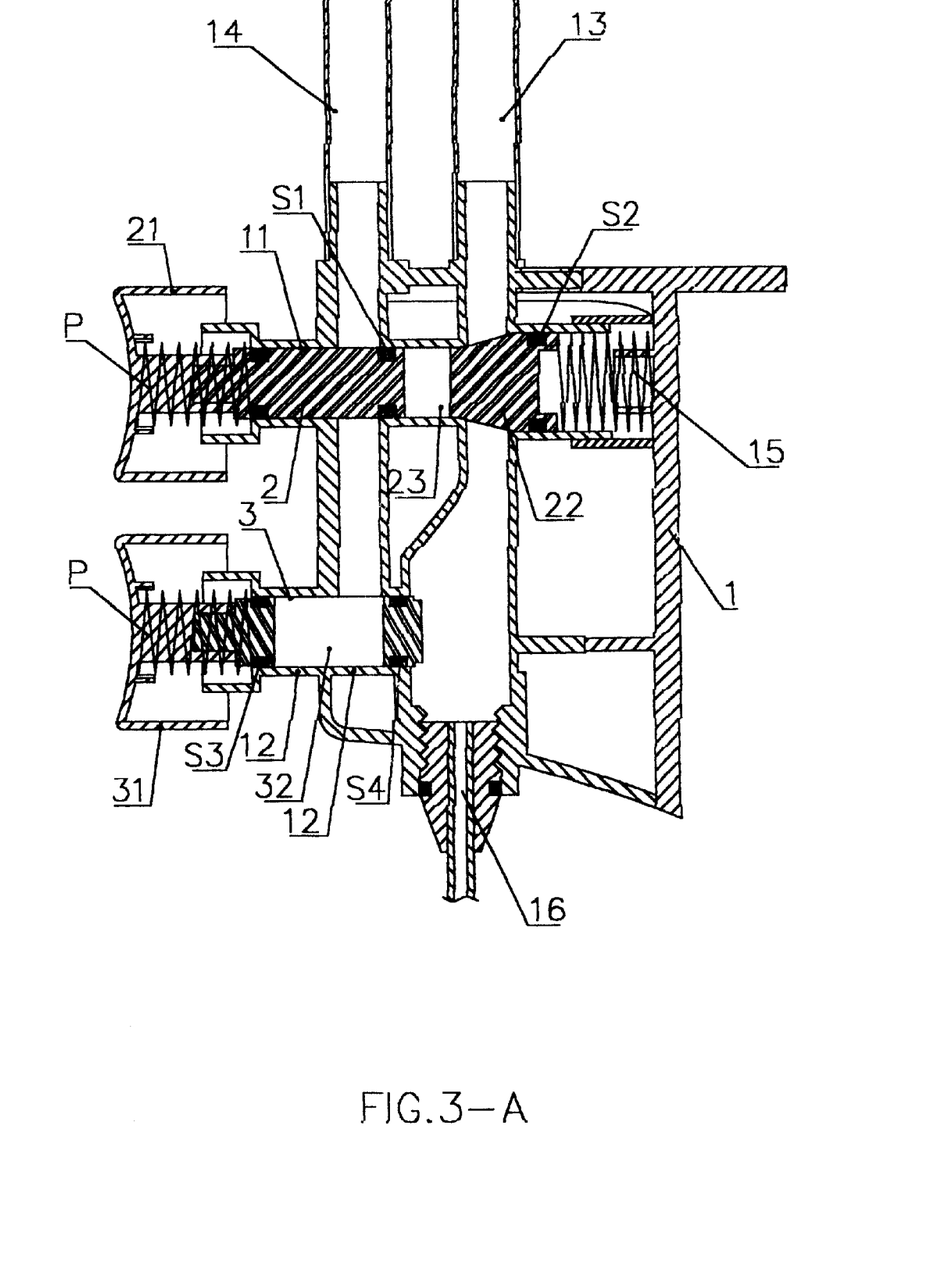

A distal end of the water pumping stud 2 is the funnel shaped tightening portion 22. The front end of the tightening portion 22 is installed with a guide hole 23 which is opened at two ends. A draining preventing washer S1 and a draining preventing washer S3 are installed aside the guide hole 23 and the tightening portion 22. In normal condition, the tightening portion 22 exactly resists against the connection of the pumping flow channel 13 and the pumping opening 11 for preventing water from flowing out from the pumping flow channel 13. The front draining preventing washer S1 exactly resists against the connection of the pumping opening 11 and the water outlet channel 14 for preventing water from draining out from the pumping opening 11 (referring to FIG. 3-A).

A surface of the water control stud 3 has a long water guide hole 32 which is opened at the two ends. The front and rear sections of the holes have draining preventing washers S3 and S4. The rear draining preventing washer S1 exactly resists against the connection of the suction opening 12 and the pumping flow channel 13 for preventing water from draining out from the suction opening 12 (referring to FIG. 3-A).

FIG. 3 shows an operation of the present invention. In surgical operation, as the affected part is desired to be washed, the water control stud 3 can be pressed downwards. The water guide hole 32 forms as a flow guide channel at the connection of the suction opening 12 and the water outlet channel 14. Thereby, water can flow into the affected part of a patient from the water outlet channel 14 through the water guide hole 32 of the water control stud 3 and the water outlet tube 16 (referring to FIG. 3-B). The dirty water after washing the affected part is pumped out. Then the water control stud 3 is released and then the water pumping stud 2 is pressed. The water pumping stud 2 resists against the elastomer 15 so that the guide hole 23 of the water pumping stud 2 exactly aligns the pumping flow channel 13 and is communicated with the pumping flow channel 13 and the water outlet tube 16. Thereby, the dirty water accumulated in the affected part can be drawn out from the water outlet tube 16 through the pumping flow channel 13 (referring to FIG. 3-C). Since the water is pumped out straightly, it is prevented that dirty water is left in some bending portions. Therefore, dirty water can be pumped out completely.

In the present invention, the water outlet channel 14 and the pumping flow channel 13 are above the main casing 1. Thus user may hold it by any hand conveniently. Therefore, the user may use the present invention by any one of the two hands alternatively.

Figure 4:
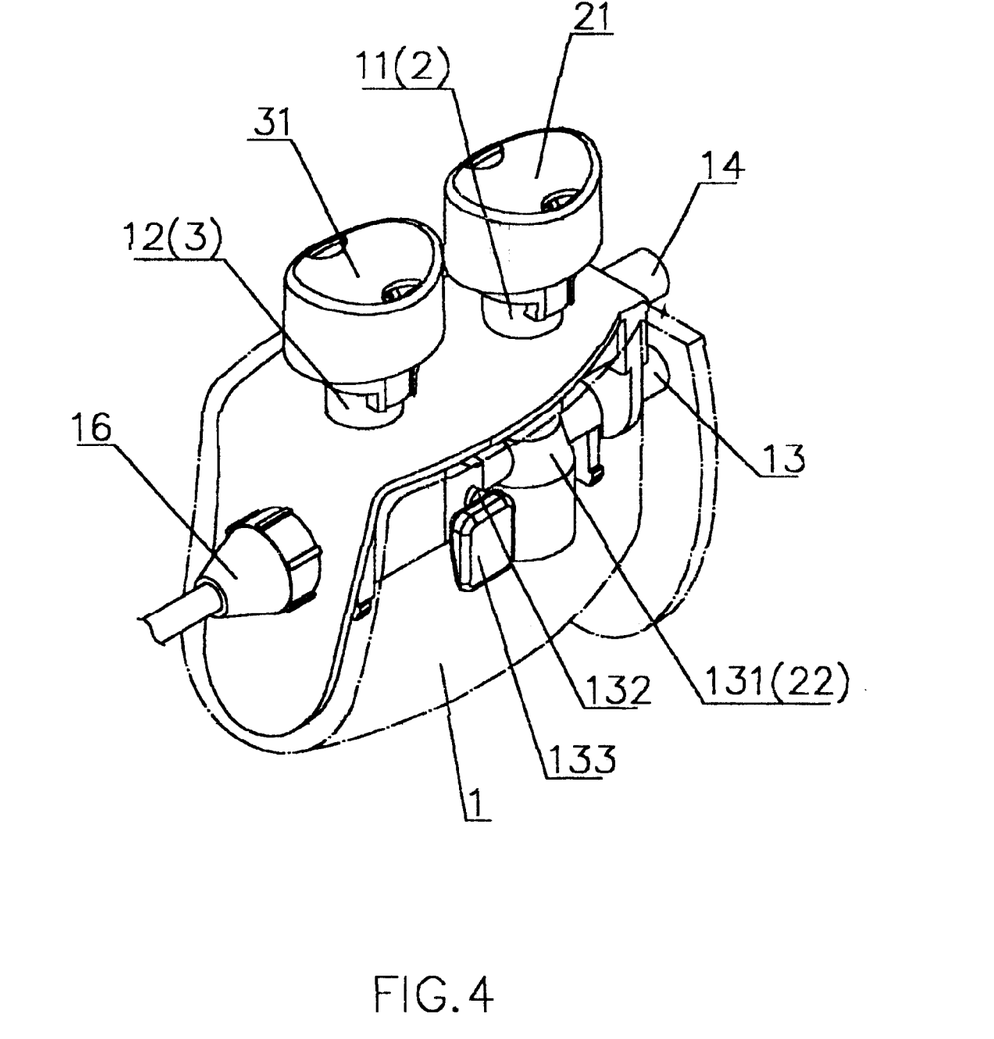
FIG. 4 shows one embodiment of the present invention, wherein a bag is installed.

Referring to FIG. 4, an embodiment shown that the present invention is installed with a bag is illustrated. In general, the medical device with patient's blood is abandoned. Since the object of the present invention is to completely pump the blood and water in tubes, a used irrigator can not be identified easily. Therefore, in the present invention, the middle section of the pumping flow channel 13 of the main casing 1 is installed with a sleeve 132 and a bag 133 is engaged with the sleeve 132. The bag 133 is installed at the flowing channel of blood and water. When blood flows through the pumping flow channel 13 to be pumped out along a straight path, some blood will flow into the bag to dirty the bag. Therefore, a used irrigator can be identified from the cleanness of the bag.

The present invention are thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An irrigator used in a celioscope surgery comprising a main casing, a water pumping stud and a water control stud which are engaged with the main casing; wherein an interior of the main casing has a pumping opening and a suction opening, and a water outlet channel and a pumping flow channel which are vertical to the pumping opening and suction opening, thereby, the water outlet channel and pumping flow channel are at an upper portion of the main casing; at an connection of the main casing and the suction opening has an elastomer in the main casing; in normal condition, the water pumping stud resists against the elastomer so as to seal the pumping flow channel; and at a lower end of the pumping flow channel has a straight water outlet tube;

the water pumping stud at the pumping opening of the main casing has a guide hole which are opened at two ends and two other ends of the guide hole facing to the water pumping stud have first draining preventing washers; when the water pumping stud is pressed downwards, the guide hole is aligned with the pumping flow channel; the first draining preventing washers exactly resists against the pumping opening and the water outlet channel for preventing that water drains out from the pumping opening; and the water control stud on the suction opening of the main casing has a long water guide hole which are opened at two ends; the water control stud has second draining preventing washers aside the two sides of the water guide holes, in normal condition, one draining preventing washer exactly resists against a connection of the pumping opening and the water outlet channel for preventing that water drains out from a connection of the water pumping stud and the pumping flow channel;

wherein by the water outlet tube at an end of the pumping flow channel, a flow channel is formed in the main casing; thereby, dirty water from the affected part of a patient is pumped out from the water outlet tube through the pumping flow channel along a straight path for preventing dirty water from being left in bending portions so as to enlarge polluted area; characterized in that a connection of the pumping flow channel and the pumping opening is a funnel shaped via hole; a distal end of the water pumping stud has a funnel shaped tightening portion; in normal condition of water pumping stud, the tightening portion exactly resists against a connection of the pumping flow channel and the pumping opening for preventing water from flowing out from the pumping flow channel; and the pumping flow channel of the main casing has a sleeve at a middle section thereof; and a bag is engaged to an opening of the sleeve; when blood and water are pumped out, part of the blood and water flows into the bag.

2. The irrigator used in a celioscope surgery as claimed in claim 1, wherein forefronts of the water control stud and the water pumping stud have a first and a second buttons, respectively; a first spring is installed between the water control stud and the first button, and a second spring is installed between the water pumping stud and the second button.

\* \* \* \* \*